US007000452B2

(12) United States Patent
Bonne et al.

(10) Patent No.: US 7,000,452 B2
(45) Date of Patent: Feb. 21, 2006

(54) PHASED MICRO FLUID ANALYZER

(75) Inventors: Ulrich Bonne, Hopkins, MN (US); Robert Higashi, Shorewood, MN (US); Cleopatra Cabuz, Edina, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/672,894

(22) Filed: Sep. 26, 2003

(65) Prior Publication Data

US 2004/0129057 A1 Jul. 8, 2004

Related U.S. Application Data

(60) Provisional application No. 60/432,220, filed on Dec. 10, 2002, provisional application No. 60/414,211, filed on Sep. 27, 2002.

(51) Int. Cl.
*G01N 19/10* (2006.01)

(52) U.S. Cl. ............... 73/23.25; 73/23.24; 73/25.01; 73/31.05; 73/863.12

(58) Field of Classification Search ............ 73/23.2, 73/31.07, 19.02, 23.35, 55.01, 23.25, 863.12, 73/31.05
See application file for complete search history.

(56) References Cited

U.S. PATENT DOCUMENTS

| | | | |
|---|---|---|---|
| 3,146,616 A | 9/1964 | Loyd | |
| 3,557,532 A | 1/1971 | Broerman | |
| 3,589,171 A * | 6/1971 | Haley | .................. 73/23.37 |
| 3,783,356 A | 1/1974 | Lide, III et al. | |
| 3,925,022 A * | 12/1975 | Showalter et al. | ............ 422/88 |
| 4,043,196 A | 8/1977 | Trageser | |
| 4,228,815 A | 10/1980 | Juffa et al. | |
| 4,324,566 A | 4/1982 | Jacob et al. | |
| 4,472,355 A * | 9/1984 | Hickam et al. | ............... 422/62 |
| 4,478,076 A | 10/1984 | Bohrer | |
| 4,483,200 A | 11/1984 | Togawa et al. | |
| 4,507,974 A | 4/1985 | Yelderman | |
| 4,576,050 A | 3/1986 | Lambert | |
| 4,735,082 A | 4/1988 | Kolloff | |
| 4,759,210 A | 7/1988 | Wohltjen | |
| 4,805,441 A * | 2/1989 | Sides et al. | ................ 73/23.25 |
| 4,909,078 A | 3/1990 | Sittler et al. | |
| 4,944,035 A | 7/1990 | Aagardl et al. | |
| 5,031,126 A | 7/1991 | McCulloch et al. | |

(Continued)

FOREIGN PATENT DOCUMENTS

DE       2 934 566 A1    3/1981

(Continued)

OTHER PUBLICATIONS

Atalla et al., "Radiation Effects with the AC Heated Strip Technique for the Measurement of Thermal Properties of Liquids", *High Temperatures—High Pressures*, vol. 17, pp. 447-452, 1985.

(Continued)

*Primary Examiner*—Hezron Williams
*Assistant Examiner*—John Fitzgerald
(74) *Attorney, Agent, or Firm*—Kris T. Fredrick

(57) ABSTRACT

A micro fluid analyzer having a concentrator and separator. A strip continuous through a channel in the concentrator may provide a hot zone that may move with the flow of fluid through the channel of the concentrator to provide a concentration of heat in the flow. A pump may provide a flow to the fluid through the analyzer. Detectors may be positioned at places where the fluid may flow. A processor or controller may be connected to the strip, separator, pump and detectors. The concentrator, separator, detectors and processor may be integrated on one chip.

14 Claims, 4 Drawing Sheets

U.S. PATENT DOCUMENTS

| | | | |
|---|---|---|---|
| 5,044,766 A | | 9/1991 | Stuart |
| 5,056,047 A | | 10/1991 | Sondergeld |
| 5,135,549 A | | 8/1992 | Phillips et al. |
| 5,146,414 A | | 9/1992 | McKown et al. |
| 5,168,746 A | * | 12/1992 | Madhusudhan et al. .... 73/23.35 |
| 5,196,039 A | | 3/1993 | Phillips et al. |
| 5,205,154 A | * | 4/1993 | Lee et al. .................. 73/23.35 |
| 5,243,858 A | | 9/1993 | Erskine et al. |
| 5,263,380 A | | 11/1993 | Sultan et al. |
| 5,268,302 A | * | 12/1993 | Rounbehler et al. .......... 436/96 |
| 5,300,758 A | * | 4/1994 | Rounbehler et al. ........ 219/497 |
| 5,313,061 A | * | 5/1994 | Drew et al. ................. 250/281 |
| 5,379,630 A | | 1/1995 | Lacey |
| 5,442,175 A | | 8/1995 | Dawson |
| 5,463,899 A | | 11/1995 | Zemel et al. |
| 5,533,412 A | | 7/1996 | Jerman et al. |
| 5,585,575 A | * | 12/1996 | Corrigan et al. ......... 73/863.71 |
| 5,587,520 A | | 12/1996 | Rhodes |
| 5,808,178 A | * | 9/1998 | Rounbehler et al. ....... 73/23.39 |
| 5,922,974 A | | 7/1999 | Davison et al. |
| 5,970,803 A | * | 10/1999 | Staples et al. ........... 73/863.12 |
| 6,016,027 A | | 1/2000 | DeTemple et al. |
| 6,131,440 A | | 10/2000 | Bertrand |
| 6,139,384 A | | 10/2000 | DeTemple et al. |
| 6,155,097 A | * | 12/2000 | Arnold ...................... 73/23.35 |
| 6,169,965 B1 | | 1/2001 | Kubisiak et al. |
| 6,178,811 B1 | | 1/2001 | Bonne et al. |
| 6,194,833 B1 | | 2/2001 | DeTemple et al. |
| 6,217,829 B1 | * | 4/2001 | Mustacich et al. ............ 422/89 |
| 6,308,553 B1 | | 10/2001 | Bonne et al. |
| 6,311,544 B1 | * | 11/2001 | Bertrand .................... 73/23.35 |
| 6,386,014 B1 | * | 5/2002 | Butch ........................ 73/23.35 |
| 6,393,894 B1 | | 5/2002 | Bonne et al. |
| 6,413,781 B1 | | 7/2002 | Geis et al. |
| 6,494,617 B1 | | 12/2002 | Stokes et al. |
| 6,497,138 B1 | * | 12/2002 | Abdel-Rahman et al. .. 73/23.42 |
| 6,497,844 B1 | * | 12/2002 | Bacaud et al. ............. 422/68.1 |
| 6,527,835 B1 | * | 3/2003 | Manginell et al. ............ 96/102 |
| 6,649,129 B1 | * | 11/2003 | Neal ........................... 422/89 |
| 6,666,907 B1 | * | 12/2003 | Manginell et al. ............. 95/87 |
| 6,732,567 B1 | * | 5/2004 | Briscoe et al. ............. 73/23.39 |
| 6,837,096 B1 | * | 1/2005 | Stewart ...................... 73/23.35 |

FOREIGN PATENT DOCUMENTS

| | | |
|---|---|---|
| DE | 32 34 146 A1 | 3/1984 |
| DE | 42 22 458 A1 | 1/1994 |
| DE | 42 43 573 A1 | 6/1994 |
| DE | 296 07 315 U1 | 9/1996 |
| DE | 196 19 133 A1 | 11/1997 |
| EP | 0 232 719 A1 | 1/1987 |
| EP | 0 348 245 A2 | 12/1989 |
| EP | 0 364 982 A2 | 4/1990 |
| EP | 0 419 873 A2 | 8/1990 |
| EP | 0 468 793 A2 | 1/1992 |
| EP | 0 702 212 A2 | 3/1996 |
| EP | 0 773 432 A2 | 5/1997 |
| GB | 2 287 792 A | 9/1995 |
| JP | 56-153256 | 11/1981 |
| JP | 57-131029 | 8/1982 |
| JP | 57-206830 | 12/1982 |
| JP | 01203970 A * | 8/1989 |
| JP | 04093648 A * | 3/1992 |
| WO | WO 92/06369 | 4/1992 |
| WO | WO 94/20825 | 9/1994 |
| WO | WO 98/22793 | 5/1998 |
| WO | WO 00/61261 | 10/2000 |

OTHER PUBLICATIONS

Atalla et al."Measurement of Thermal Properties of Liquids with an AC Heated-Wire Technique", *Interational Journal of Thermophysics*, vol. 2, No. 2, 1981.

Bonne et al., "Industrial Wireless PHASED Sensor Phase 1. Feasibility Demonstration," Progress Report for 4th Quarter of 2002, pp. 1-17, Jan. 31, 2002.

Bonne, et al., "PHASED: a Faster, Smarter and More Affordable Gas Analysis Device," 16th International Forum on Process Analytical Chemistry, San Diego, CA., Jan. 22-25, 2002, pp 1-17.

Bonne, U., et al., "New Gas Composition and Trace Contaminant Sensors," GTI Natural Gas Technologies Conference, Orland, FL, Sep. 30-Oct. 2, 2002, pp. 1-12.

Cabuz, C. et al., "Mesoscopic Sampler Based on 3-DF Arrays of Electrostatically Actuated Diaphragms," Proc. 10th Conf. S.S. S&A. Transducers '99 Jun. 7-12, 1999, Sendai, Japan.

Cabuz, C., et al., "The Dual Diaphragm Pump," IEEE, pp. 519-522, 2001.

Dipl.-Ing. Dr. techn. Wolfgang Wehrmann et al., "Korrelationstechnik", *Expert Verlag*, Grafenau, XP002094984, 173 pages, 1980.

Fuggerth, Endre, "Zone Gas Chromatography," Analytical Chemistry, 61, No. 14, pp. 1478-1485, (1989).

Honeywell Electronic Materials Interconnect Solutions, Thin Films—Dielectrics, Comparison of Solution and Film Properties, Advanced Products for IC Fabrication, 1 page. http://www.advanced-polymers.com/star_center/techincal_papers/reduction_in_effective_dielectric_constant.pdf, 1 page.

http://www.chrompack.com/cgi/applicsview?ap=A00607&Go=G0, NexTrieve document view, 2 pages, printed Dec. 26, 2002.

http://www.zoex.com/html/technote_kt030505-1.html, Zoex Corporation, "A New Window on the Che," 5 pages, printed Mar. 15, 2004.

International Search Report, PCT/US00/19924, mailed Mar. 5, 2001, 7 pages.

Kenndler, Ernst, "Gas Chromatography," Institute for Analytical Chemistry, University of Vienna, pp. 1-34, Sep. 9, 1999.

Kindlund et al., "Quartz Crystal Gas Monitor With Gas Concentrating Stage," Sensors and Actuators, 6 (1984) pp. 1-17.

NexTrieve document view, http://www.chrompack.com/cgi/applicsview?ap=A00764, 2 pages.

Park, et al., "Microdischarge Arrays: A New Family of Photonic Devices (Revised)," IEEE Journal on Selected Topics in Quantum Electronics, vol. 8, No. 2, pp. 387-394, Mar./Apr. 2002.

Park, et al., "Photodetection in the visible, ultraviolet, and near-infrared with silicon microdischarge devices," Applied Physics Letters, vol. 81, No. 24, pp. 4529-4531, Dec. 9, 2002.

Park, et al., : Arrays of silicon micro discharge devices with multicomponent dielectrics, Optics Letters, vol. 26, No. 22, pp. 1773-1775, Nov. 15, 2001.

Phillips, J.B. et al., "Thermal Modulation: A Chemical Instrumentation Component of Potential Value in Improving Portability," Field Analytical Chemistry and Technology, 1(1): 23-29, 1996.

Quimby, et al., "Evaluation of a Microwave Cavity, Discharge Tube, and Gas Flow System of Combined Aas Chromatography—Atomic Emission Detection," Analytical Chemistry, vol. 62, No. 10, pp. 1027-1034, May 15, 1990.

Stevenson, Robert, "Wintergreen '97," The World of Separation Science, The 19th International Symposium on Capillary Chromatography and Electrophoresis, 11 pages.

Toker et al., "Design and development of a fiber optic TDI CCD-based slot-scan digital mammography system," X-ray Detector Physics and Applications II, Proceedings SPIE—The International Society for Optical Engineering, vol. 2009 (Jul. 13-14, 1993) pp. 246-252.

Whitman et al., "Double-Injection FIA Using First-Order Calibration for Multicomponent Analysis," Analytical Chemistry 63 (1991) pp. 775-781.

* cited by examiner

20-Element Pre-Concentrator,  Diff. TC,  20-Element Separator

PHASED MICRO FLUID ANALYZER

This application claims priority under 35 U.S.C. § 119(e)(1) to, now abandoned, U.S. Provisional Patent Application Ser. No. 60/414,211, filed Sep. 27, 2002, and entitled "PHASED SENSOR", wherein such document is incorporated herein by reference. This application also claims priority under 35 U.S.C. § 119(e)(1) to co-pending U.S. Provisional Patent Application No. 60/432,220, filed Dec. 10, 2002, and entitled "PHASED-II SENSOR", wherein such document is incorporated herein by reference.

The U.S. Government may have rights in the present invention.

BACKGROUND

The invention pertains to detection of fluids. Particularly, the invention relates to such detection with concentrator and separator devices. More particularly, it pertains to the detection of fluids with integrated devices.

Aspects of structures and processes related to gas sensors may be disclosed in U.S. Pat. No. 6,393,894, issued May 28, 2002, and entitled "Gas Sensor with Phased Heaters for Increased Sensitivity," which is incorporated herein by reference, and in U.S. Pat. No. 4,944,035, issued Jul. 24, 1990, and entitled "Measurement of Thermal Conductivity and Specific Heat," which is incorporated herein by reference.

SUMMARY

Multi-gas detection and analysis may be automated via affordable, in-situ, ultra-sensitive, low-power, low-maintenance and compact micro sensors and analyzers. A micro gas micro analyzer incorporating a phased heater array, concentrator and separator contributes to the availability of a low-cost multi-gas analyzer.

The present micro analyzer may be low-power, fast, compact, low cost, intelligent, wireless, low maintenance, robust and highly sensitive. A vast portion of the micro analyzer may be integrated on a chip with conventional semiconductor processes or micro electromechanical machined system (MEMS) techniques. The fabrication of about 1-$\mu$m-thick membranes as GC-column structure (see further details below) may result in low-power consumption, fast, compact and in situ placement of the micro analyzer. The flow rate of the air or gas sample through the sensor may be very small. Further, a carrier gas for the samples is not needed and eliminates the associated maintenance and bulk of pressurized gas-tank handling. This approach permits the sensor to provide quick analyses and prompt results, maybe at least an order of magnitude faster than some related art devices. It avoids the delay and costs of labor-intensive laboratory analyses. The sensor is intelligent in that it may have an integrated microcontroller for analysis and determination of gases detected, and may maintain accuracy, successfully operate and communicate information in and from unattended remote locations. The phased micro analyzer is, among other things, a lower-power, faster, and more compact, more sensitive and affordable version of a gas chromatograph.

The present micro analyzer may involve fabrication, connection, switching and control of a continuous heater film that is energized not by discrete heater element steps, but by a continuous but short heat pulse that is made to travel at about the same speed as that of the sample gas. One may improve the continuous but one-side-of-channel heater plus adsorber film with one covering the whole internal wall of a dielectric-material capillary of high internal surface/volume ratio. The analyte concentration wave may be shaped by sizing the heater element to optimize peak width and height in relation to the detector size and natural desorption wave width. There may be elimination of the artistry of related-art GC films by the application of a repeatable, compatible, thermally cyclable and patternable film, according to a semiconductor industry-grade process.

DESCRIPTION

Figure 1:
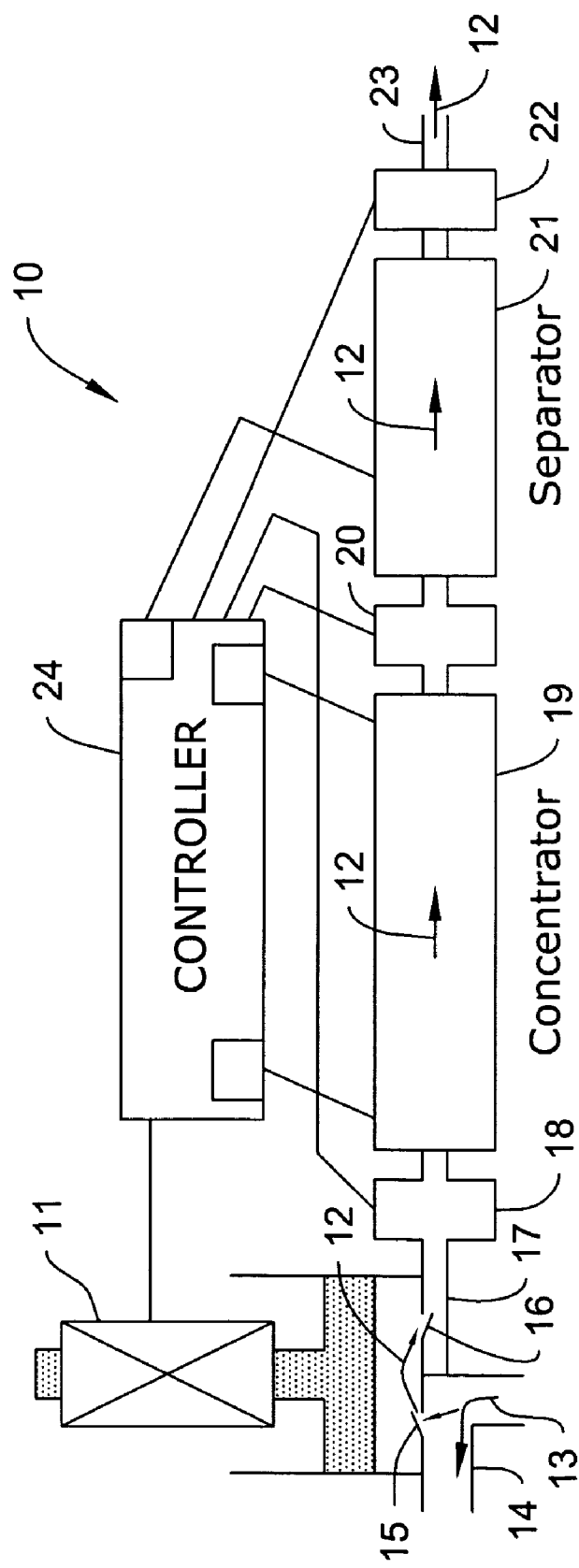
FIG. 1 is a diagram of an illustrative example of the continuous phased fluid micro analyzer.

FIG. 1 shows an example of a fluid sensor system 10. A pump 11 may draw a sample 12 from a fluid flow 13 in pipe, tube or fluid conveying mechanism 14. "Fluid" is a generic term that includes liquids and gases as species. For instance, air, gas, water and oil are fluids. Pump 11 may be a solenoid pump or another kind of pump for pulling sample fluid 12 in through valve 15 and pushing fluid 12 out through valve 16 into tube 17 or the like. Fluid may pass through a thermal conductivity detector 18 and into a concentrator 19. From concentrator 19, fluid 12 may go through a thermal conductivity detector 20 and into a separator 21. From separator 21, fluid 12 may go through a thermal conductivity detector 22. From detector 22, fluid 12 may be exited from system 10 through a tube 23 or the like back into the place that contains fluid 13 or other appropriate place. Detectors 18, 20 and 22 may not all be present in system 10, or there may be other kinds of detectors and different arrangements as needed for a particular fluid testing. There may be a microcontroller 24 connected to pump 11, detectors 18, 20 and 22, concentrator 19 and separator 21. Controller 24 may cause pump 11 to function as needed at a desired rate, receive inputs from detectors 18, 20 and 22, and send operating signals to concentrator 19 and separator 21. Example physical dimensions of concentrator 19 may include a length of about 50 centimeters and an inside diameter of about 100 microns. Separator 21 may have dimensions about the same as those of concentrator 19.

Figure 2:
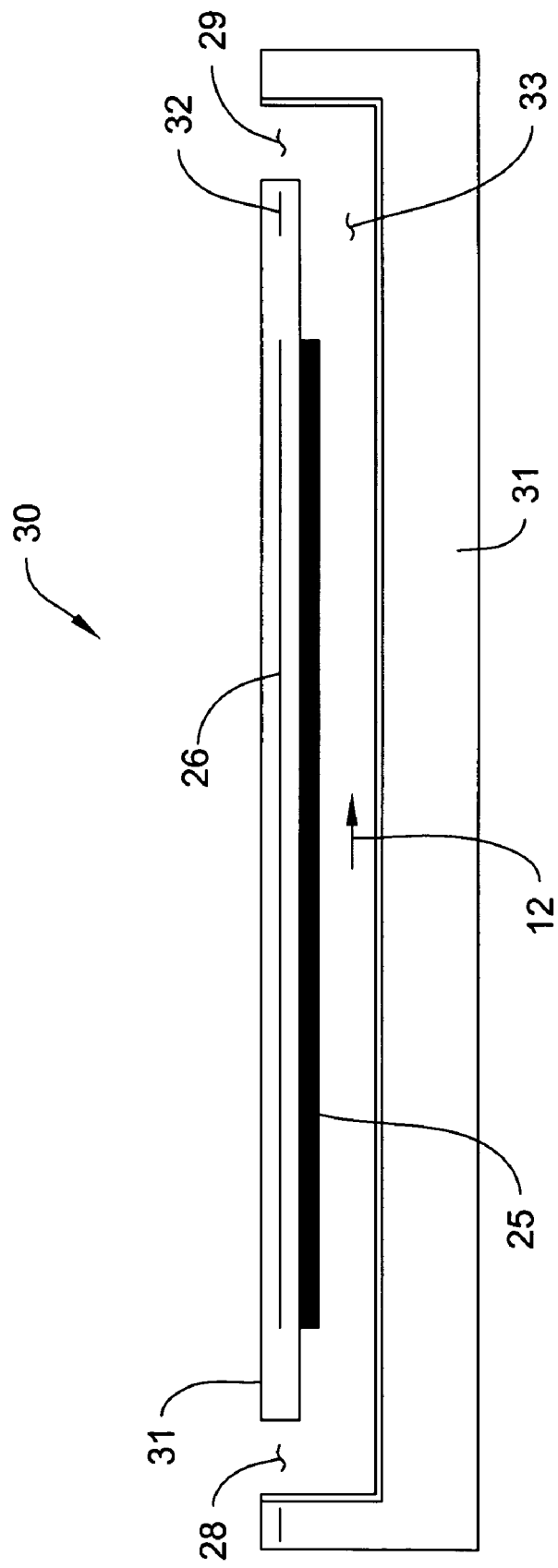
FIG. 2 shows a continuous heater strip for providing the heat pulse.
Figure 3:
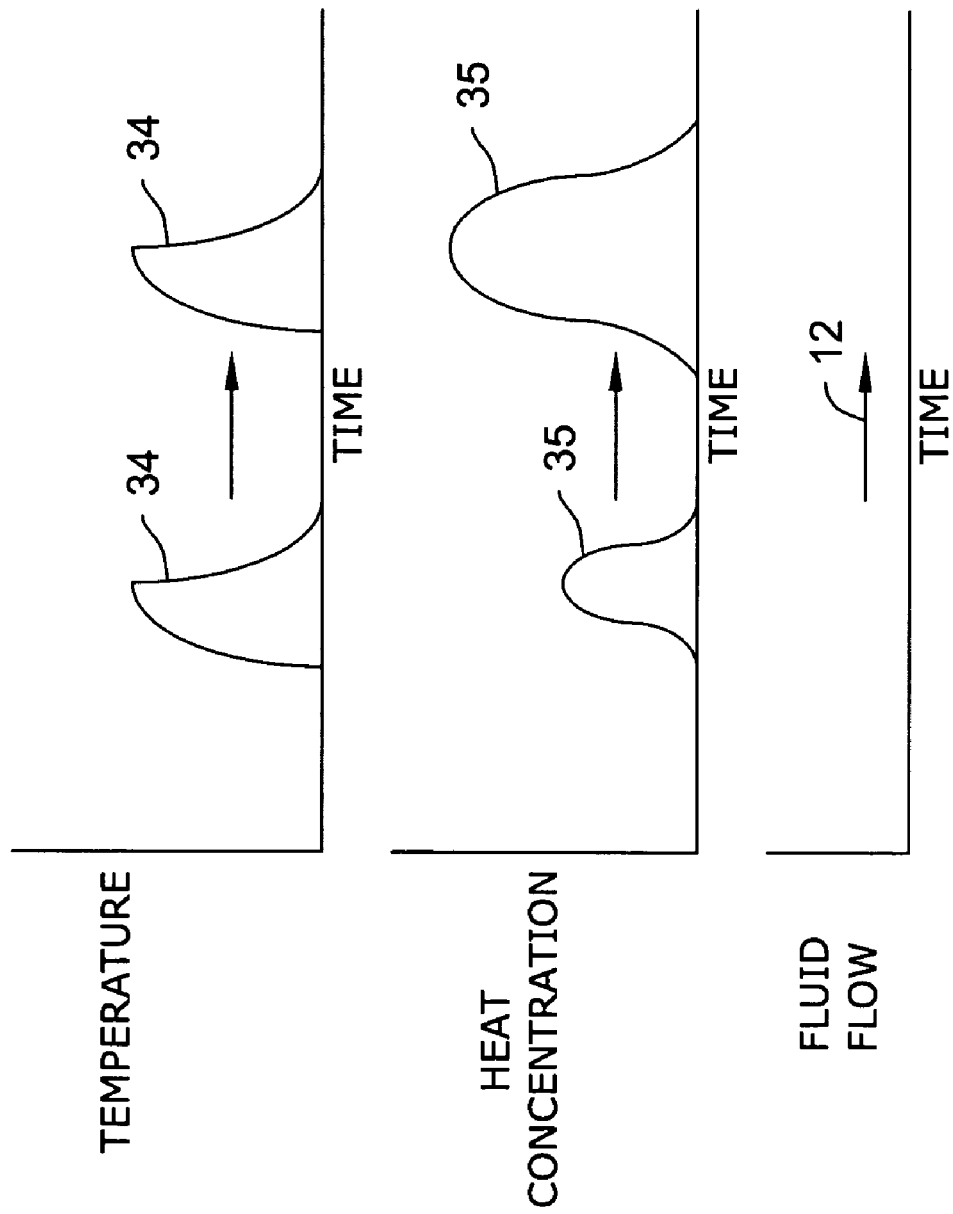
FIG. 3 is a timing graph.

A mechanism 30 for heating sample fluid 12 may have a continuous heater film 25 as shown in FIG. 2. The electronics in controller 24 may output operational signals to heater element 26 for the generation of a traveling heat pulse, hot-band or hot-zone 34 on continuous heater film 25. Hot-zone or pulse 34 is shown in FIG. 3 as moving relative to time on film 25. The terms pulse, band, zone or appropriate descriptive terms may be used interchangeably. Coinciding with hot-zone 34 is a representation of a heat concentration 35 in fluid 12 as fluid 12 moves at the same rate in the same direction as hot-zone 34. As fluid 12 moves down channel 33, its heat concentration 35 increases. Film 26 and element 26 may be situated in support structure 31. Fluid 12 may flow into inlet 28 through channel 33 adjacent to heater film 25 and be heated. Fluid 12 may exit channel 33 through outlet 29. The flow of fluid 12 may be at the same rate of movement as that of the hot-zone 34. One concept for its implementation may require the synthesis of a package of a series of sine-wave currents, which cancel each other except at the delta-function-like hot-zone 34; as the offset of the sine waves is made to increase, so will the distance of the hot-zone 34 advance from the beginning to the end of heater film 25. The rate of advance of the offset and hot-zone 34 are made to be about equal to the average sample gas or fluid 12 speed in flow channel 33. The dynamics associated with such a delta-function synthesizer may be equivalent to the motion of a water wave generator in a trough to generate a standing wave somewhere in the middle of the trough, with due allowance for reflected wave effects. However, after establishing such a speed-controlled hot-zone 34, the benefits of the improved pre-concentration (as in a multi-element heater array with infinite number of elements) would be increased analyte concentration, reduced peak width and reduced fabrication cost.

An alternate approach for generating hot zone 34, besides by microwave synthesis of a moving delta-function in a delay line, may involve scanning IR/visible light beams from an arc, hot filament or laser source(s) rather than by moving or stationary heaters, or by streams of cooled and heated air.

The ratio of the channel-fluid/adsorber-film volumes may be referred to as the β-factor. A small β-factor may make for a more effective and sensitive column, since there would be an increased adsorber-film volume relative to the channel-fluid volume. By moving to a pre-concentrator design with larger adsorber surface, the β-factor value may be improved, whether the heater plus adsorber coating is applied to the whole internal diameter of a capillary. The β-factor may be improved with a square- or star-shaped cross section for attaining a still smaller β-value. Continuous heater 25 described may enable one to energize such a structure. Triangular, square and/or star-shaped cross sections can be made via extrusion of polymer fibers of Honeywell International Inc. of Morristown, N.J.

An alternative to the forced desorption via the ideal, continuous, traveling hot-zone 34 may be an array of heater elements whose lengths may be fixed but not equal to each other. This may involve optimizing heater element dimensions. For instance, the heater array may consist of one very long heater 26 (~10–30 cm) followed by a much shorter heater (~0.2–1 mm or 2 to 10 d, with d=diameter of channel 33 of ~0.1 mm) that may accumulate all of the pre-concentrated analyte before "injection" into TCD 20 (thermal conductivity detector) between the end of concentrator 19 and the inlet to separator 21. This may involve an easier assembly with fewer heaters. However, significant power may be needed to heat almost the whole concentrator 19 simultaneously. On the other hand, the array could consist of 10–20 medium-sized heater elements (~1–5 cm) to collect and concentrate the analyte and 1–3 short ones (~0.2–1 mm) to "focus" and "inject" a so optimized pulse into the following separator 21 and TCD 20. A combination of the preceding approaches may be used. The last heater element in the structure, one or a few short element(s), might even feature a thermo-electrically (TE) cooled element (to minimize any loss of analyte) before it is rapidly heated to provide the final "injector" pulse.

Figure 4:
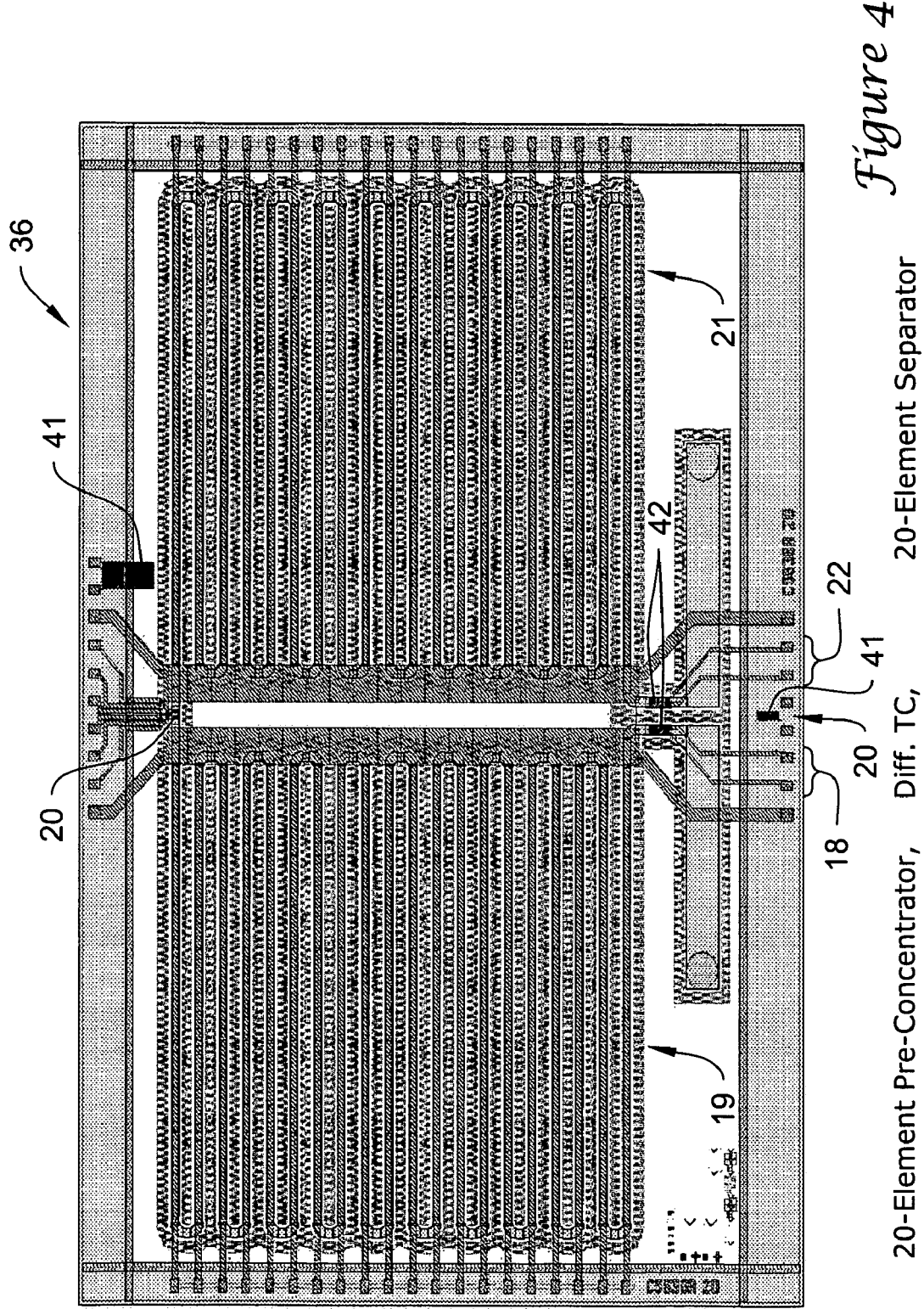
FIG. 4 is a basic layout of an integrated circuit that includes a concentrator, a separator, and detectors.

An optimization of system 10 may include integration of the TCD-Concentrator-TCD-Separator-TCD elements on one chip as in FIG. 4 to maximize the effectiveness of the pulse injection operation and the detection function.

As to the adsorber coating, most GC (gas chromatography) adsorber coatings are proprietary to GC supplier houses, such as Supelco™, Chrompack-Varian™ and Restek™, and their fabrication relies on the skill and trade secrets of their staff. For the present sensor system 10, one may use a particular class of coatings of "Spin-On Glasses" offered and marketed by Honeywell International Inc. One such glass may be Nanoglass® E, which has a porosity near 40%, pore sizes in the 20 Å range, and surface areas of 800–900 $m^2/g$, similar to high-quality GC coatings.

In sum, system 10 may use a continuous heater mechanism 30. A traveling and short hot-zone 34 (electrical delta function) may be used on heatable adsorber strip 25 to obtain continuous sample gas analyte concentration augmentation, rather than using an array of discrete heater elements. An arbitrary heater profile in space and time may be used for the separator 21. Hot zone 34 may be generated via microwave synthesis of a moving delta-function in a delay line, or via scanning IR-visible light beams from an arc, hot filament or laser sources.

High-surface adsorber channels may be effected by a use of capillaries with fully-coated internal surfaces (rather than the one-sided film) of channel 33 having a round, square of even star-shaped cross section, to increase the concentrating and the speed of the separating operation (i.e., a large surface enables the use of thinner and faster GC films).

The use of an array of heater elements whose lengths may be fixed but not equal to each other, and may include elements featuring TE-cooling and TE- or R-heating; to maximize preconcentration and/or concentration, minimize power use, optimize injection pulse, yet minimize number of elements, complexity and cost. The envisioned optimization may even include integration of the TCD-Concentrator-TCT-Separator-TCD elements to maximize the effectiveness of the pulse injection operation.

As to film material, one may use any one of Honeywell International Inc.'s many types of "Spin-On Glass" coating material to provide the GC adsorber film. Acceptable materials may include the open-pore, functionalized for hydrophobicity Nanoglass®E or the polymeric "GX-3P" or poly-methyl-siloxane type of SOG compounds offered by Honeywell and others, functionalized for the desired level of polarity.

An effective concentrator 19, inside a capillary column (steel or silica), may have first a deposit of a 0.1 to 1 micron film of low-TC porous glass or polymer (e.g., via pumping liquid solution through it, blowing the excess out and baking), followed by a heater metal film deposition (e.g., via mirror solutions), followed by a final GC film of porous glass or polymer. This approach combines more surface area with thermal isolation for rapid, low-power heating.

For cleaning, in case a high-boiling analyte material condenses and accumulates on the non-heated walls of the sensor structure, it may be helpful to periodically heat the whole channel support 31 wafer as well as the heater element(s) 26 while purge gas is flowing through channel 33.

The advantages of continuous heater strip 25 are that it may be easier to fabricate (with less labor), more reliable (having fewer wire bonds or contacts), more controllable (length of heated zone 34 may be controlled) and lower cost (because of no or fewer FET switches needed) of electrically connecting concentrator 19 and separator 21 heater film strip 25 to a power supply.

One may have a high adsorber-film/sample fluid flow channel volume (even with thin adsorber film thickness) which may enable greater speed of response of system 10. For film material, the spin-on glass or polymer materials are proven and reproducible products, which can be deposited in the desired thickness range (0.1 to 0.8 $\mu$m) that can be patterned. The optimizing concentrator 19 and separator 21 heater elements may maximize pre-concentration, minimize power use, optimize the injection pulse, and yet minimize the number of elements, and complexity and cost.

System 10 may have separate chips for concentrator 19 and for separator 21, as well as an off-chip flow sensor which may be regarded as detector 18, 20 and/or 22. However, such fabrication design requires plumbing connections for the sample and analyte flow 12 between these two chips having concentrator 19 and separator 21, respectively, and the risk of losing the focused and concentrated analyte volume during this transfer. Further, this design keeps the two parts of the differential thermal conductivity type gas sensor 10 apart, which may lead to significant noise levels. Another design of micro analyzer 10 layout and fabrication may integrate the sensing, concentrating and separating elements (18, 19, 20, 21 and 22) on a single chip 36, as shown in FIG. 4. The latter design may significantly reduce noise levels and thereby improve signal-to-noise ratios. Also, the wafer-level assembly of micro analyzer 10 in FIG. 4 may significantly lower fabrication costs relative to a separate chip assembly.

The layout of system 10 in FIG. 4 shows how an integration of the concentrator 19, separator 21 and detectors 18, 20 and 22, may benefit especially a single differential thermal conductivity detector (with its two elements 18 and 22 now side by side at the inlet and outlet of the sample fluid stream 12, of which there was a separate pair before, on each chip, a flow sensor 20 which can now measure the passing ("electronic") injection of a heat concentrated analyte slug 35 (FIG. 3) into separator 19, a temperature sensor (and possibly pressure sensors and flow control device) useful for predicting the average fluid velocity of the concentrated analyte slug 12 moves through concentrator 19. Thermal conductivity detectors 18 and 22 may result in a differential thermal conductivity detector 42. There may be temperature sensors 41 on chip 36.

The present fluid micro analyzer may have an on-one-chip integrated operations of concentration, flow sensing (and control), separation, differential thermal conductivity detection, and temperature and pressure sensing. The mounting and wire-bonding the micro analyzer chip might not be directly onto the PCB motherboard but onto a connected small daughter PCB to enable exchange of new chips without damage to the motherboard PCB.

The advantages of the on-one-chip 36 approach include no broadening of the analyte slug 12 during transfer from concentrator 19 to separator 21, the ability to sense the passage of the analyte slug 12 at the end of concentrator 19, an improved signal-to-noise ratio by virtue of no broadening of slug 12 between concentrator 19 and separator 21 and smaller temperature change disturbances between the two thermal conductivity (TC) sensing elements 18 and 22. Other advantages include the possibility to also add and integrate inlet and outlet absolute pressure sensors to determine speed of the analyte slug 12 as it moves through heating element and the daughter PCB-approach which also enables connection of differently-sized fluid analyzer heater chips with one mother PCB.

Although the invention has been described with respect to at least one illustrative embodiment, many variations and modifications will become apparent to those skilled in the art upon reading the present specification. It is therefore the intention that the appended claims be interpreted as broadly as possible in view of the prior art to include all such variations and modifications.

What is claimed is:

1. A fluid analyzer comprising:
a pump;
a concentrator fluidly connected to the pump; and
a separator fluidly connected to the concentrator; and
wherein the concentrator comprises a channel and a continuous heater film along the channel; and
a controller coupled to the continuous heater film for generating a moving heat pulse in the heater film that moves down the heater film and thus the channel, the moving heat pulse defined by a peak temperature with lower temperatures both downstream and upstream of the peak temperature.

2. The analyzer of claim 1, wherein the moving heat pulse has a rate of movement approximately the same as a fluid moving through the channel.

3. The analyzer of claim 2, further comprising:
a first detector situated between the pump and the concentrator; and
a second detector situated at an output of the separator.

4. The analyzer of claim 3, further comprising a third detector between the concentrator and the separator.

5. The analyzer of claim 4, wherein:
the first detector is a thermal conductivity detector;
the second detector is a thermal conductivity detector; and
the third detector is a flow sensor.

6. The analyzer of claim 5, wherein the controller is also connected to the pump, separator and detectors.

7. A fluid analyzer, comprising:
a channel for receiving a gas;
a continuous heater film extending along at least part of the channel;
a controller coupled to the heater film for generating a moving heat pulse that moves down the continuous heater film and thus the channel, the moving heat pulse defined by a peak temperature with lower temperatures both downstream and upstream of the peak temperature.

8. The fluid analyzer of claim 7 further comprising a detector positioned downstream of the heater film.

9. The fluid analyzer of claim 7, wherein the moving heat pulse has a rate of movement that is approximately the same as the gas moving through the channel.

10. A method for operating a fluid analyzer having a channel, comprising:
providing a gas down the channel, wherein the channel includes a continuous heater film extending along at least part of the channel;
generating a moving heat pulse in the continuous heater film that translates down the continuous heater film and thus the channel, the moving heat pulse defined by a peak temperature with lower temperatures both downstream and upstream of the peak temperature.

11. The method of claim 10, wherein the moving heat pulse has a rate of movement that is approximately the same as the gas moving through the channel.

12. A fluid analyzer, comprising:
a channel for receiving a gas;
a first heater element thermally coupled to the channel;
a second heater element thermally coupled to the channel, wherein the second heater element is downstream of the first heater element and has a length along the channel that is less than the first heater element;
a controller coupled to the first heater element and the second heater element, wherein the controller heats the first heater element, and a predetermined time later, heats the second heater element.

13. The fluid analyzer of claim 12 wherein the predetermined time is related to rate of movement of the gas through the channel.

14. The fluid analyzer of claim 13 wherein the second heater element is positioned adjacent to an output of the channel.

* * * * *